United States Patent
Surti

(10) Patent No.: US 8,114,045 B2
(45) Date of Patent: Feb. 14, 2012

(54) APPARATUS AND METHODS FOR DELAYING GASTRIC EMPTYING TO TREAT OBESITY

(75) Inventor: Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 617 days.

(21) Appl. No.: 12/041,337

(22) Filed: Mar. 3, 2008

(65) Prior Publication Data

US 2008/0221595 A1 Sep. 11, 2008

Related U.S. Application Data

(60) Provisional application No. 60/904,471, filed on Mar. 2, 2007.

(51) Int. Cl.
*A61M 5/00* (2006.01)
*A61F 2/04* (2006.01)

(52) U.S. Cl. .......................................... 604/9; 623/23.68

(58) Field of Classification Search ................ 604/8–10, 604/151; 623/1.24, 1.26, 2.1, 2.26, 23.68; 606/151
See application file for complete search history.

(56) References Cited

U.S. PATENT DOCUMENTS

| 4,580,568 A | 4/1986 | Gianturco |
| 5,562,697 A | 10/1996 | Christiansen |
| 5,820,584 A | 10/1998 | Crabb |
| 6,302,917 B1 | 10/2001 | Dua et al. |
| 6,540,789 B1 | 4/2003 | Silverman et al. |
| 6,544,291 B2 * | 4/2003 | Taylor ........................ 623/23.68 |
| 6,740,121 B2 | 5/2004 | Geitz |
| 6,746,489 B2 | 6/2004 | Dua et al. |
| 6,802,868 B2 | 10/2004 | Silverman et al. |
| 6,994,095 B2 | 2/2006 | Burnett |
| 7,037,343 B2 | 5/2006 | Imran |
| 7,090,699 B2 | 8/2006 | Geitz |
| 7,122,058 B2 | 10/2006 | Levine et al. |
| 2004/0122526 A1 * | 6/2004 | Imran ........................ 623/23.65 |
| 2005/0055039 A1 | 3/2005 | Burnett et al. |
| 2005/0228504 A1 | 10/2005 | Demarais |
| 2005/0273060 A1 | 12/2005 | Levy et al. |
| 2006/0161139 A1 | 7/2006 | Levine et al. |
| 2008/0140099 A1 | 6/2008 | Ghabrial et al. |
| 2010/0305590 A1 | 12/2010 | Holmes et al. |

OTHER PUBLICATIONS

Wiley Encyclopedia of Biomedical Engineering, Copyright 2006 John Wiley & Sons, Inc., entitled "STENTS" by C. Lally, D.J. Kelly, P.J. Prendergast—pp. 1-10.
International Search Report & Written Opinion dated Sep. 22, 2008 (PCT/US2008/055665).

* cited by examiner

*Primary Examiner* — Leslie Deak
*Assistant Examiner* — Philip R Wiest
(74) *Attorney, Agent, or Firm* — Brinks Hofer Gilson & Lione

(57) ABSTRACT

Medical devices and methods for the treatment of obesity. The medical devices generally include an attachment portion for attaching the medical devices on or adjacent the pylorus and a limitation portion for limiting the passage of stomach contents through the pylorus to delay emptying the stomach. The limitation portion may be responsive to pressure from stomach contents to substantially close or to open the passageway.

9 Claims, 6 Drawing Sheets

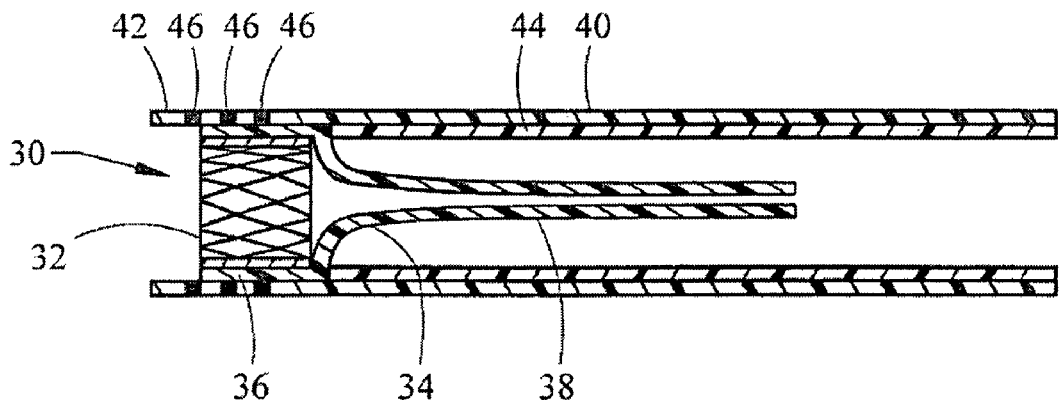
Fig. 2a
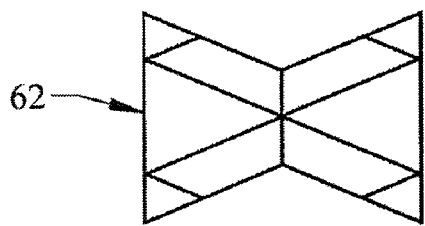
Fig. 2b
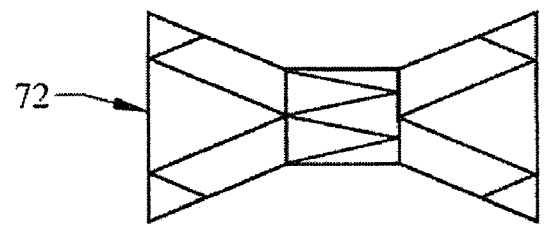
Fig. 2c
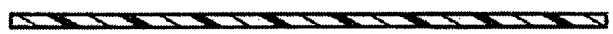
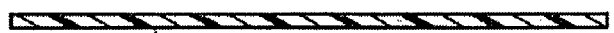
Fig. 2d
Fig. 2e

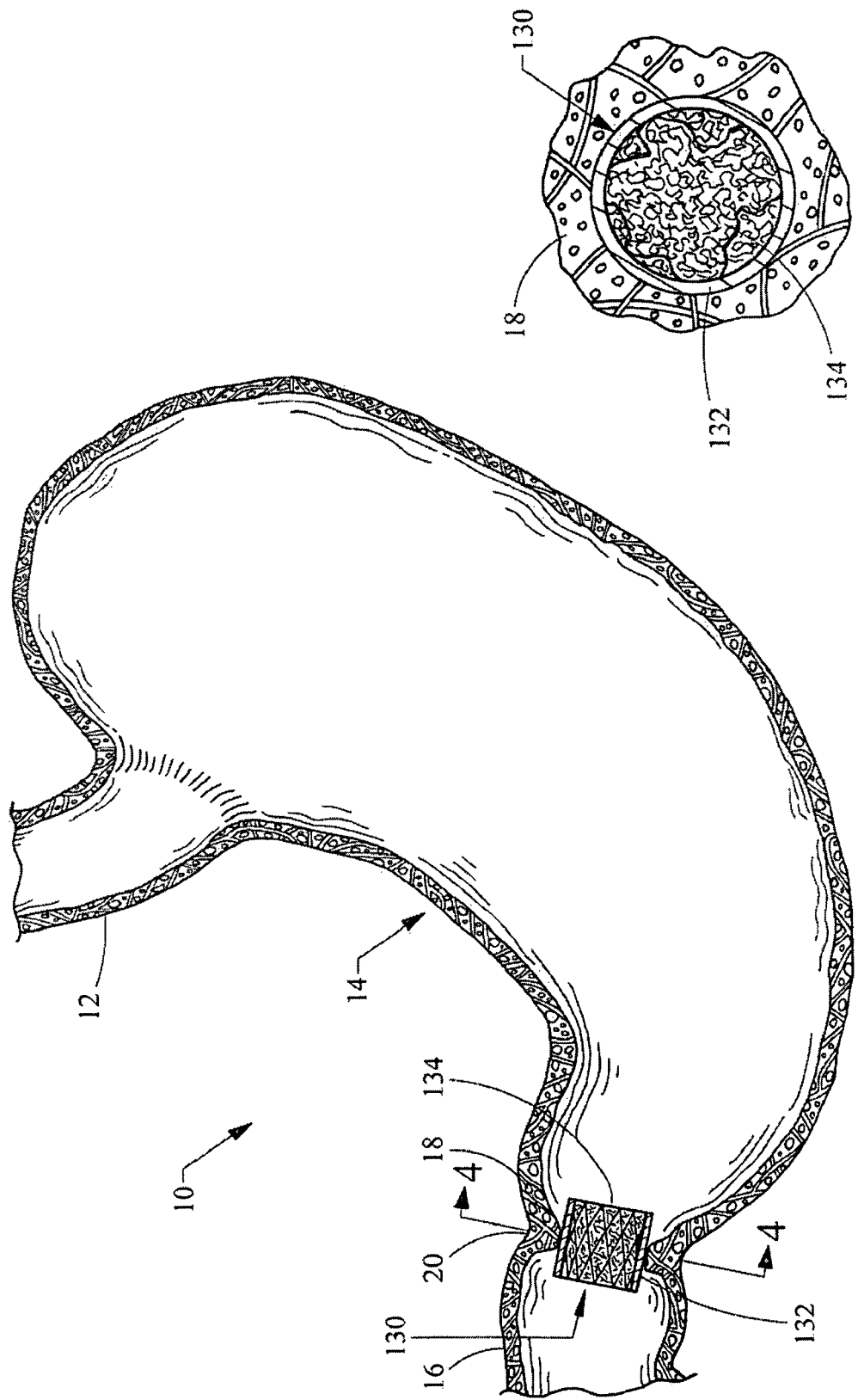

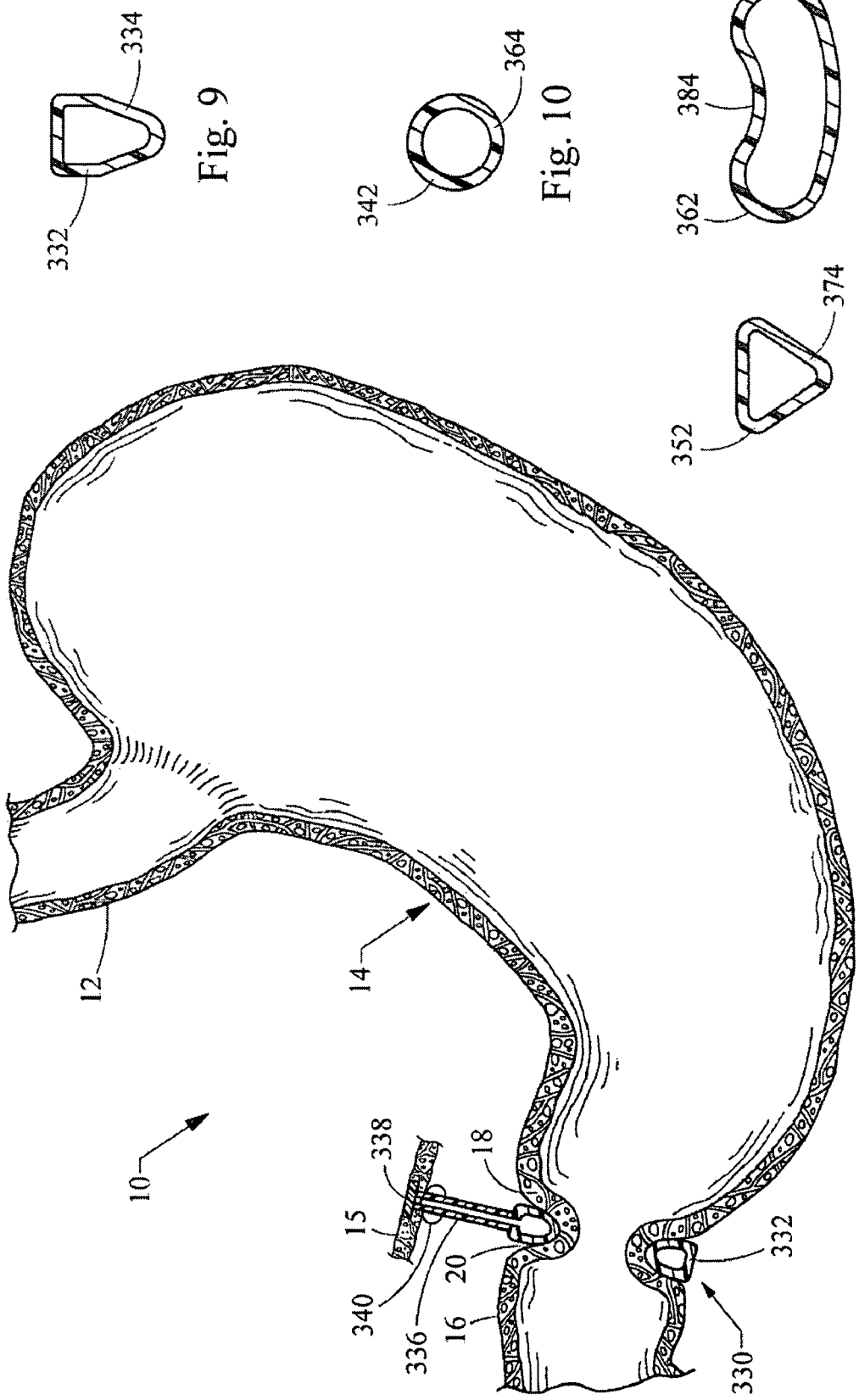
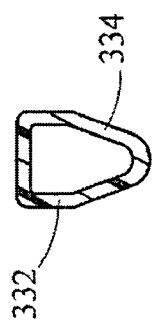
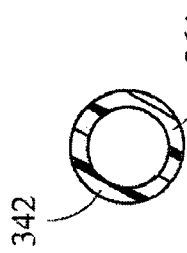
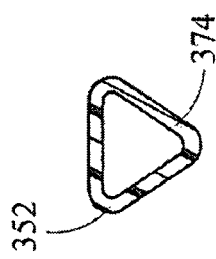
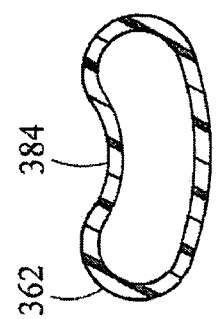
Fig. 8
Fig. 9
Fig. 10
Fig. 11
Fig. 12

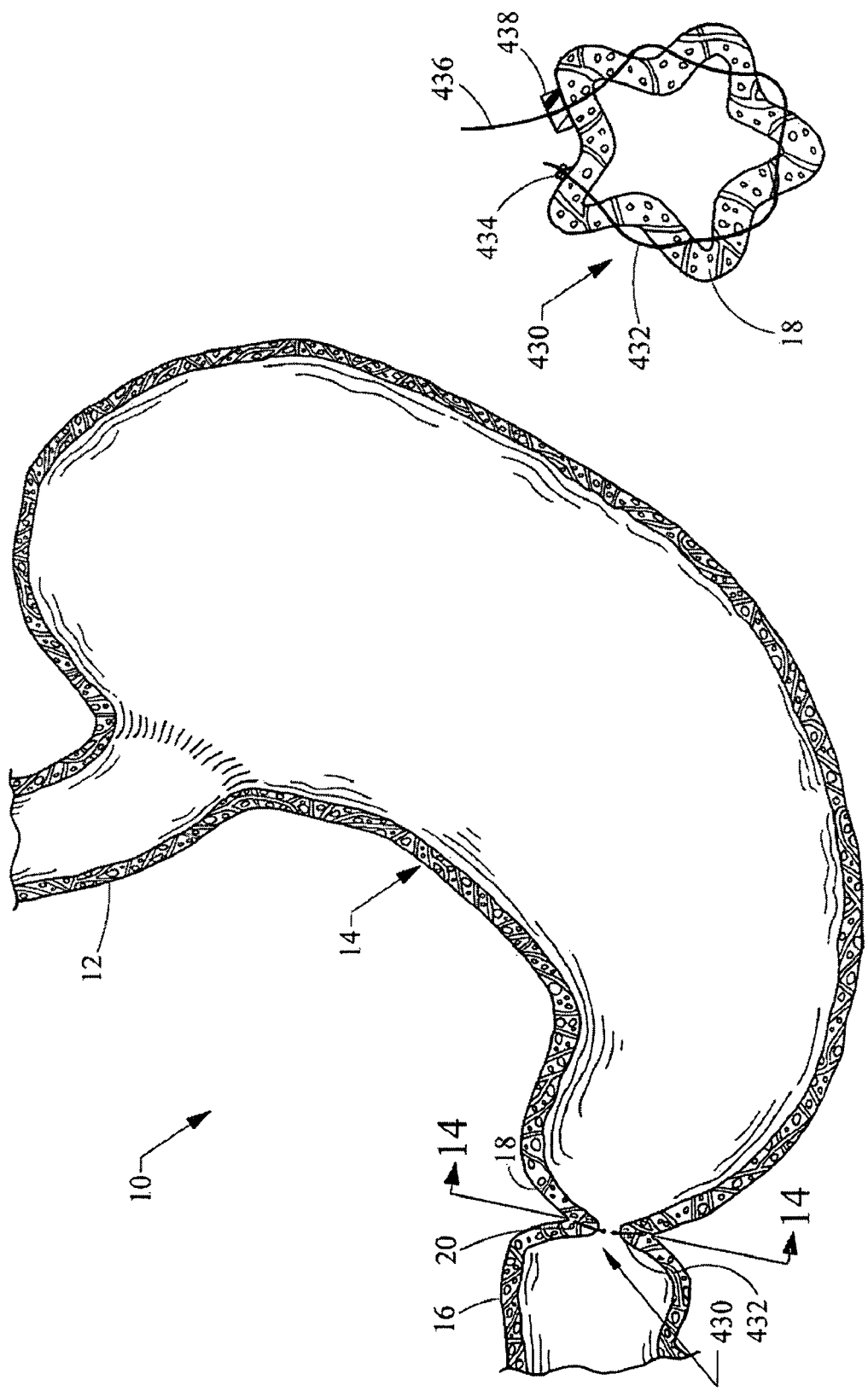

APPARATUS AND METHODS FOR DELAYING GASTRIC EMPTYING TO TREAT OBESITY

CROSS-REFERENCE TO RELATED APPLICATIONS

This application claims the benefit of U.S. Provisional Application Ser. No. 60/904,471 filed on Mar. 2, 2007, entitled "APPARATUS AND METHODS FOR DELAYING GASTRIC EMPTYING TO TREAT OBESITY" the entire contents of which are incorporated herein by reference.

FIELD OF THE INVENTION

This invention relates to medical devices, and more particularly to obesity treatment devices that can be placed near the stomach of a patient to delay gastric emptying.

BACKGROUND OF THE INVENTION

It is well known that obesity is a very difficult condition to treat. Methods of treatment are varied, and include drugs, behavior therapy, and physical exercise, or often a combinational approach involving two or more of these methods. Unfortunately, results are seldom long term, with many patients eventually returning to their original weight over time. For that reason, obesity, particularly morbid obesity, is often considered an incurable condition. More invasive approaches have been available which have yielded good results in many patients. These include surgical options such as bypass operations or gastroplasty. However, these procedures carry high risks, and are therefore not appropriate for most patients.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These balloons are typically cylindrical or pear-shaped, generally range in size from 200-500 ml or more, are made of an elastomer such as silicone, polyurethane, or latex, and are filled with air, water, or saline. While some studies demonstrated modest weight loss, the effects of these balloons often diminished after three or four weeks, possibly due to the gradual distension of the stomach or the fact that the body adjusted to the presence of the balloon. Other balloons include a tube exiting the nasal passage that allows the balloon to be periodically deflated and re-insufflated to better simulate normal food intake. However, the disadvantages of having a inflation tube exiting the nose are obvious.

BRIEF SUMMARY OF THE INVENTION

The present invention provides medical devices and methods for the treatment of obesity which delay gastric emptying, resulting in food remaining in the stomach longer causing the individual not to each as much. The medical devices are well tolerated while also being easy to place and retrieve. The medical devices generally include an attachment portion for attaching the medical devices to the interior or exterior surface of on the pylorus (or a body structure adjacent the pylorus) and a limitation portion for limiting the passage of stomach contents through the pylorus to delay emptying the stomach. In several embodiments, the attachment portion is a stent, preferably an expandable stent, and most preferably a self-expanding stent. The limitation portion in one embodiment is a sleeve of flexible material attached to the stent. The sleeve may take many forms, but preferably is responsive to pressure from stomach contents to substantially close the passageway. In another embodiment, the limitation portion is a mesh member connected to the stent. The mesh member is collected in a manner to make a passageway through the pylorus tortuous.

In other embodiments, the attachment portion is an inflatable ring sized to be positioned adjacent the pylorus. For example, the inflatable ring may be positioned around the exterior surface of the pylorus and inflated to constrict the size of the passageway through the pylorus. Here, an inflation tube is fluidically connected to the inflation ring and includes a valve that is preferably accessible from the exterior of the body.

In yet another embodiment, the attachment portion is a deflectable ring sized to be positioned adjacent the pylorus. The limitation portion preferably includes a flexible valve connected to the deflectable ring. The flexible valve may be a simple disk extending across the opening defined by the pylorus, the disk including an opening allowing passage of stomach contents therethrough. The disk is structured to flex and adjust the size of the opening in response to pressure from stomach contents. Numerous valve configurations may be readily employed.

In yet another embodiment, the pylorus may be sutured to reduce the size of the passageway therethrough. The suture is preferably passed through the pylorus set at least two locations, and most preferably is woven in a purse string fashion to assist in constricting the pylorus.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 2a is a cross-sectional view of a delivery device for deploying the medical device depicted in FIG. 1;

FIGS. 2b and 2c depict various geometries of stents forming a portion of the medical device depicted in FIG. 2a;

FIGS. 2d and 2e depict various constructions of the flexible sleeve forming a portion of the medical device depicted in FIG. 1 and FIG. 2a;

FIG. 3 is a cross-sectional view of the stomach having another embodiment of the medical device constructed in accordance with the teachings of the present invention;

FIG. 4 is a cross-sectional view of the medical device depicted in FIG. 3;

FIG. 8 is a cross-sectional view of a stomach having another embodiment of a medical device for the treatment of obesity constructed in accordance with the teachings of the present invention;

FIGS. 9-12 are cross-sectional views depicted in various constructions of the medical device depicted in FIG. 8;

FIG. 13 is a cross-sectional view of a stomach having another embodiment of a medical device for the treatment of obesity constructed in accordance with the teachings of the present invention; and FIG. 14 is another cross-sectional view of the medical device depicted in FIG. 12.

DETAILED DESCRIPTION OF THE INVENTION

Figure 1:
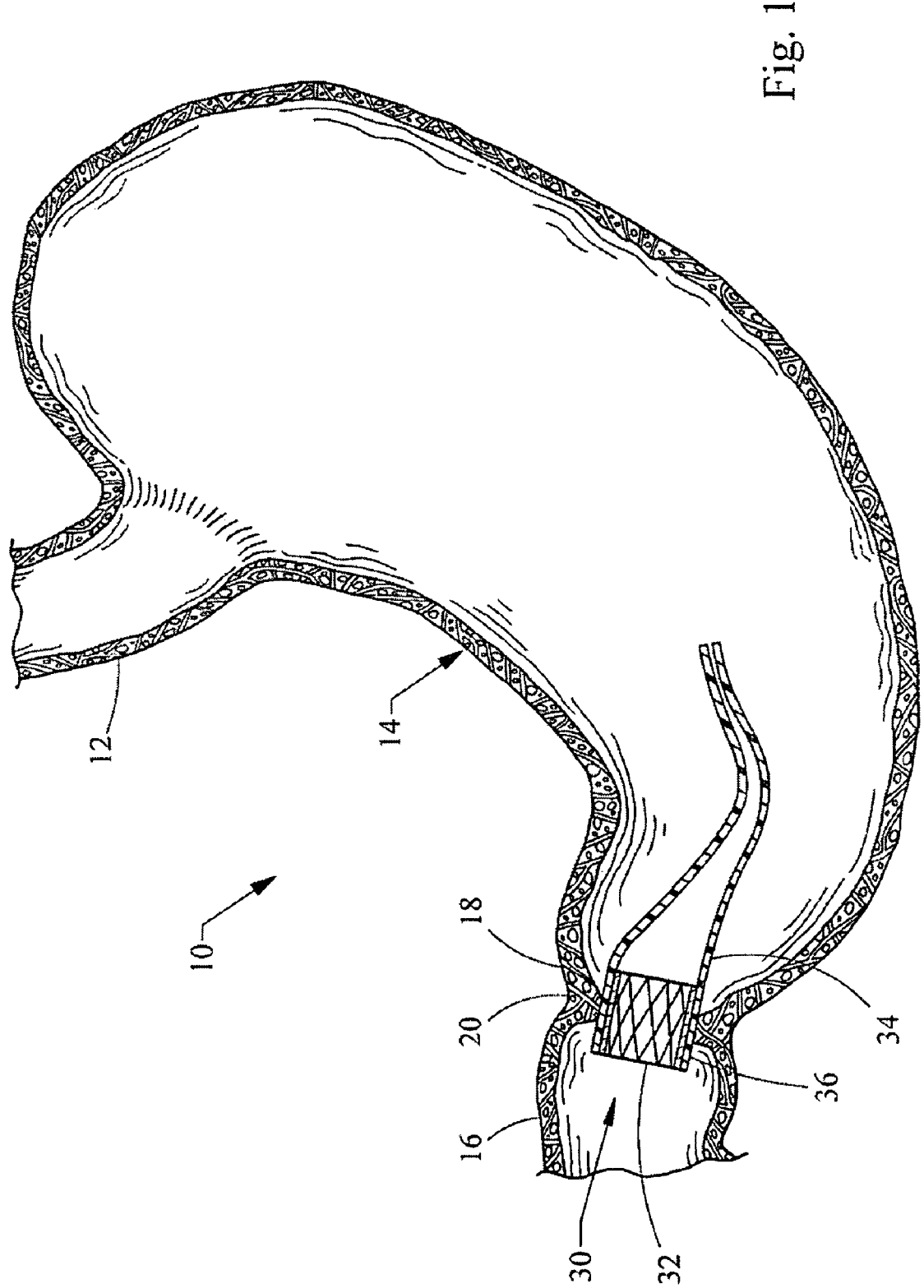
FIG. 1 is a cross-sectional view of a stomach having one embodiment of a medical device for the treatment of obesity constructed in accordance with the teachings of the present invention.

Turning now to the figures, FIG. 1 depicts one embodiment of a medical device 30 for the treatment of obesity constructed in accordance with the teachings of the present invention. Generally depicted is a portion of the gastro-intestinal tract 10 having the esophagus 12 leading to the stomach 14, which in turn leads to the duodenum 16 (i.e. the upper portion of the small intestines). The pylorus 18 defines the passageway between the stomach 14 and duodenum 16 and includes a pyloric sphincter 20 for controlling the passage of stomach contents into the intestines. In order to delay emptying of the contents of the stomach 14 to the intestines, the medical device 30 is positioned proximate the pylorus 18 for delaying emptying of the stomach contents. As used herein, "pylorus" generally refers to the area of the opening from the stomach 14 to the duodenum 16, and includes locations both upstream (proximal) of the pyloric sphincter 20 and downstream (distal) of the pyloric sphincter 20.

The medical device 30 can be referred to as a pylorus plug and includes a stent 32 and a sleeve 34 attached to the stent 32. A distal end 36 of the sleeve 34 is attached to the stent 32 using conventional methods such as suturing or bonding. The stent 32 is preferably an expandable stent, and most preferably a self-expanding stent such as the zig-zag wire metal stents of the Gianturco type as described in U.S. Pat. No. 4,580,568, the disclosure of which is incorporated by reference herein in its entirety. As such, the stent 32 may be collapsed into a deployment configuration within a delivery sheath 40, as shown in FIG. 2a. A distal end 42 of the delivery sheath 40 is positioned adjacent the pylorus 18, which preferably includes radiopaque markers 46 to assist with placement. A pusher 44 is fitted within the deployment sheath 40, and relative translation between the delivery sheath 40 and pusher 44 will cause the medical device 30 and stent 32 to be positioned beyond the distal end 42 of the delivery sheath 40, where it can expand to engage the interior surface of the pylorus 18.

It will be readily apparent to those skilled in the art that numerous types of stents and delivery systems may be employed in conjunction with the present invention. For example, the stent 32 may be a balloon expandable stent or a simple tubular stent (in which the outer diameter of the stent would be selected to correspond with the size of the pyloric sphincter 20 to maintain its position with in pylorus 18). Likewise, the stent 32 may have numerous types of geometries, such as coil designs, open cell designs, multi-cell closed-cell designs, and woven designs. The geometric shapes of the stent 32 may also be of various contractions such as cylindrical (FIG. 2a), butterfly shape 62 (e.g. made by two tapering stents connected together as shown in (FIG. 2b), or bow-tie shape 72 (e.g. two tapering stents interconnected by a cylindrical stent as shown in FIG. 2c), to name a few. An outer or inner sheath may be used to connect multiple stents, as is known in the art. Although not a requirement, it is preferable that the stent 32 or other attachment means is deflectable, such that it may radially expand and contract to correspond with natural expansion and contraction of the pyloric sphincter 20.

Turning back to FIG. 1, the sleeve 34 is connected to the stent 32 and extends proximally therefrom into the stomach 14. The sleeve 34 is constructed of a flexible plastic which will collapse and fold down on itself in response to pressure from the stomach 14. At the same time, the material of the sleeve 34 must have sufficient rigidity to prevent inversion of the sleeve (i.e. passing through the stent 32 and extending distally into the duodenum 16). The sleeve 34 may have a generally cylindrical configuration as shown in FIGS. 1 and 2d, or a tapered (such as a frustoconical shape) configuration 64 as shown in FIG. 2e.

The sleeve is constructed to act somewhat similarly to a one-way valve, whereby the passageway through the pylorus 18 is normally closed, but will open when the pressure in the duodenum 16 is greater than the pressure in the stomach 14 (which is normally not the case). In actuality, however, the sleeve 34 will at times be partially open (i.e. the tubular configuration of sleeve 34 will be substantially collapsed) such that passage of contents in the stomach 14 through the pylorus 18 and into the duodenum 16 does occur, albeit at a much slower rate. As such, delayed gastric emptying is achieved and weight loss may be obtained by increasing the time during which the stomach 14 is full, giving the patient a feeling of fullness and preventing the desire to over eat.

It will also be recognized that the medical device 30 may be employed in a condition where the flexible sleeve 34 extends distally into the duodenum 16. Especially when the sleeve 34 tapers as shown in FIG. 2e, the medical device 30 is operative to reduce the size of the opening through the pylorus 18 to delay emptying of the stomach.

Turning now to FIGS. 3 and 4, another embodiment of a medial device 130 for treatment of obesity is constructed in accordance with the teachings of the present invention. As with the previous embodiment, the medical device 130 comprises a pylorus plug having a stent 132 for attaching the device to the pylorus 18. In this embodiment, a collection of mesh material 134 is fitted inside the interior of the stent 132. As used herein, "mesh" or "mesh material" refers to an open material, fabric or structure having a plurality of spaced apart openings. Many types of mesh materials may be employed including interwoven strands, composites such as filter materials, or indigestible materials formed as a mesh through the creation of spaced apart openings. Many well-known plastics have suitable properties for forming the mesh member 134 including polyesters, polyurethanes, polyethylenes, polyamides, silicone or other possible materials. Preferably, the mesh member 134 is digestive-resistant, meaning the material is not subject to the degradive affects of stomach acid and enzymes, or the general environment found within the gastric system over an extended period of time. This allows the device to remain intact for the intended life of the device. This does not necessarily mean that the material cannot be degraded over time; however, one skilled in the medial arts and gastrological devices would readily appreciate the range of material that would be suitable for use as a long-term intragastric member.

The mesh member 134 is formed in a manner to limit the passage of stomach contents through the pylorus 18 and delay emptying of the stomach. The mesh member 134 may effectively reduce the cross-sectional area through which the contents may pass, and/or makes the passageway tortuous to delay gastric emptying. In one form, the mesh member 134 may include a strip of mesh material that is collected in a birds-nest manner, or the strip may be folded in a more organized manner. It will be recognized by those skilled in the art that many methods of collecting various forms of mesh material to form the mesh member 134 may be readily employed to limit the passage of stomach contents through the pylorus 18.

As with the previous embodiments, numerous types of stents 132 may be employed, and likewise many different means for attaching the mesh member 134 to the pylorus 18 may be used. For example, the mesh member 134 may be directly stitched to the pyloric wall. Similarly, the mesh member 134 may be attached to the stent 132 in many manners, such as through stitching, adhesives, bonding techniques such as plastic welding or mechanical fasteners. For example, the mesh material 134 could include its own tubular sheath which in turn is connected to the stent 132. It will be apparent that these techniques can be employed on other embodiments, as well.

Figure 6:
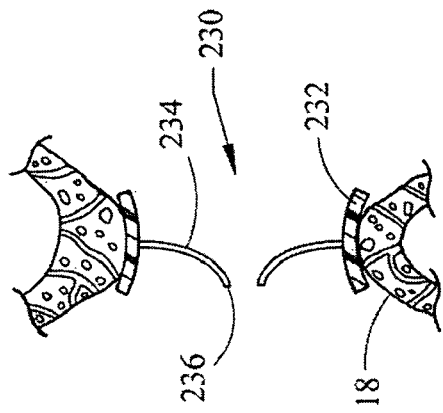
FIG. 6 is an enlarged cross-sectional view showing operation of the medical device depicted in FIG. 5.
Figure 7:
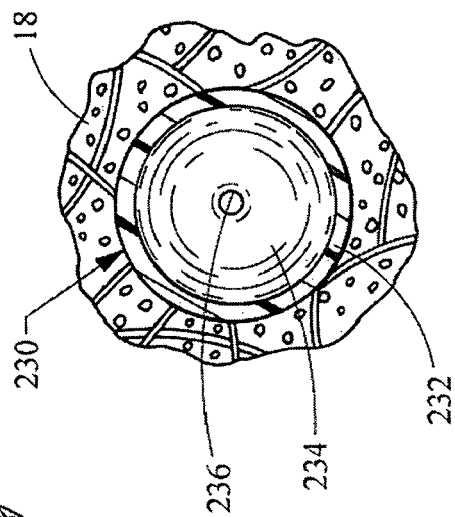
FIG. 7 is a another cross-sectional view of the medical device depicted in FIG. 5.
Figure 5:
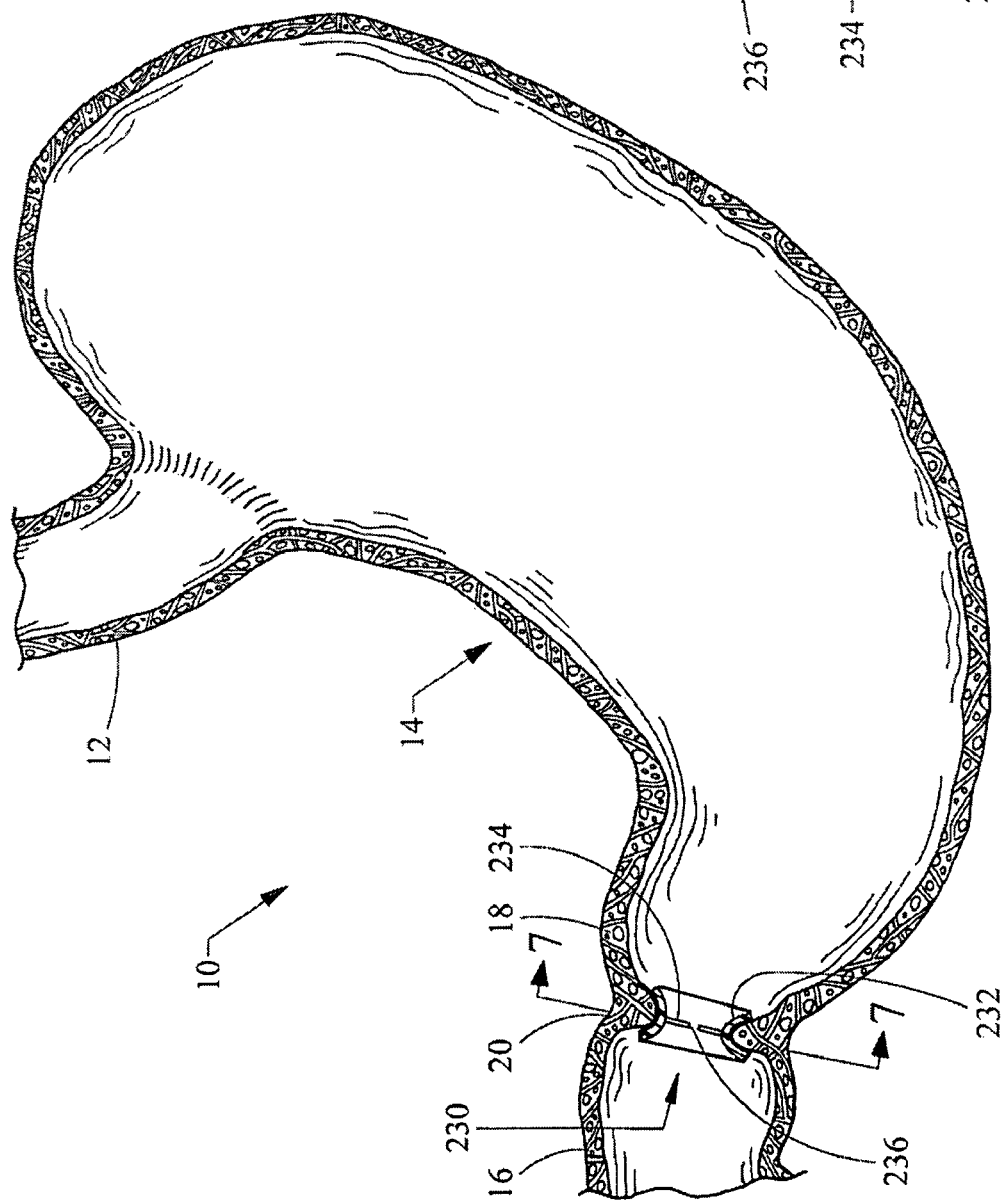
FIG. 5 is a cross-sectional view of a stomach having another medical device for the treatment of obesity constructed in accordance with the teachings of the present invention.

Turning to FIGS. 5-7, another embodiment of a medical device 230 has been depicted positioned within the pylorus 18 for treating obesity in accordance with the teachings of the present invention. The medical device 230 takes the form of a pylorus plug having a deflectable ring 232 which extends around and engages the interior surface of the pylorus 18. The ring 232 may have many cross-sectional shapes, but is preferably arranged to be fitted at the pyloric sphincter 20 and remain connected to the same. Suturing or other supplemental connecting features may also be employed. Preferably, the deflectable ring 232 is sufficiently flexible to allow natural expansion and contraction of the pyloric sphincter 20 while remaining connected thereto.

The medical device further includes a valve 234 which is connected to the deflectable ring 232. As depicted, the valve 234 simply comprises a membrane or flexible disc extending across the opening defined by the pylorus 18 and the delectable ring 232. The flexible valve 234 includes a opening 236 which allows passage of stomach contents therethrough. It will be recognized that the area of opening 236 is substantially smaller than the typical area of the pylorus 18 and pyloric sphincter 20. As best seen in FIG. 6, the flexible valve 234 deflects in response to the pressure of contents within the stomach 14. As the flexible valve 234 deflects, the opening 236 is capable of enlarging to increase the amount of stomach contents which can pass to the intestines. Although a simple flexible membrane or disc 234 having an opening 236 has been depicted, it will be recognized by those skilled in the art that numerous types of valves may be employed to limit the passage of stomach contents through the pylorus 18, including mechanical valves, flexible valves, one-way valves, flapper valves and the like.

Turning now to FIGS. 8-11, another embodiment of a medical device for treating obesity has been depicted in accordance with the teachings of the present invention. In this embodiment, the medical device 330 includes an inflatable ring 332 sized to be positioned adjacent the pylorus. The inflatable ring 332 is sized to be fitted around the exterior surface of the pylorus 18. The inflatable ring 332 is designed to receive an inflation material such as a liquid (i.e. saline) or gas (i.e. air) and is expandable to decrease the inner diameter of the ring 332. As such, the ring 332 may be inflated to exert a radially inward force on the pylorus 18 to reduce the size of the opening defined by the pylorus 18, and thereby delay the emptying of contents from the stomach 14 to the intestines (i.e. duodenum 16). Through use of the valve 338, the reduction in size of the opening through the pylorus 18 may be infinitely adjusted as desired through the inflation or deflation of the ring 332.

The radially inward portion of the inflatable ring 332 is preferably tapered to better accommodate the shape of the exterior surface of the pylorus 18. For example, as shown in FIGS. 9-11, the radially inward portions 334, 364, 374 have been shown as tapered. In these figures, it will also be seen that the cross-sectional shape of the inflatable ring 332 may take many forms such as the house-shape in FIG. 9, the circular shape in FIG. 10 or the generally triangular shape in FIG. 11, although numerous shapes will be readily apparent to those skilled in the art.

Preferably, an inflation tube 336 is fluidically connected to the inflatable ring 332, and leads to a valve 338 which may be positioned at skin level of the patient, such as by fixing the valve 338 to the abdominal wall 15 of the patient. The inflation tube 336 may include an inflation balloon 340 proximate the valve 338 for this purpose. Alternatively, the inflation tube 336 and valve 338 may be left within the patient for percutaneous access, endoscopic access or the like. It will also be recognized that the inflatable ring may be fitted to the interior wall of the pylorus 18, the cross-section of such a ring 362 being depicted in FIG. 12. In this case, the radially outward portion 384 of the inflatable ring 362 preferably includes an indentation or other shape designed to receive the pylorus 18 and pyloric sphincter 20 therein. Again, many possible cross-sectional shapes are possible for such an inflatable ring 362 in addition to the kidney-shape shown in FIG. 12.

A final embodiment of the medical device 430 for the treatment of obesity, constructed in accordance with the teachings of the present invention, has been depicted in FIGS. 13 and 14. In this embodiment, a suture 432 has been passed through the pylorus 18 to reduce the size of the opening through the pylorus and delay emptying of the stomach 14. The suture 432 is passed through the pylorus 18 at least two locations, and preferably is passed through the pylorus 18 in a purse string fashion best seen in FIG. 14. A distal end 434 may be attached to the pylorus 18 such as through a simple knot or other fastener or anchor, allowing the proximal end 436 of the suture 432 to be retracted to tension of the purse string and reduce the size of the opening through the pylorus 18. A suture lock 438 or other fastener may likewise be used to hold the suture 432 in place and maintain the reduced size of the pylorus 18. It will be recognized by those skilled in the art that numerous methods of suturing, as well as methods of fastening or other fastening devices, may be employed in order to reduce the size of the opening through the pylorus 18.

In view of the foregoing embodiments, it will be readily apparent that numerous variations and combinations of a means for positioning the medical device adjacent the pylorus 18, combined with a limitation means for limiting the passage of stomach contents through the pylorus, are possible. For example, the attachment means may include, but are not limited to, a stent, a flexible ring, an inflatable ring, or suture material, and may also include various mechanical structures such as deployable frames, tissue anchors or staples, and adhesives. Similarly, the limitation means may include, but are not limited to, elongated sleeves of material, mesh material, valves, expandable rings or balloons, suture material or other physical objects that can be used to reduce the size of the opening through the pylorus which may or may not be deflectable. The limitation means may or may not be responsive to the pressure within the stomach 14 to adjust the rate of flow of stomach content to the small intestine.

A method for treating obesity is also provided in accordance with the teachings of the present invention. The method generally includes providing a pylorus plug such as one of the pylorus plugs previously described. Generally, the pylorus plug has a passageway therethrough that is constructed to delay the emptying of contents from the stomach to the intestines. The pylorus plug is delivered to a location proximate the pylorus 18. Delivery devices such as pushing catheters, guide wires, and actuation cables may be utilized to translate the pylorus plug through an overtube or delivery sheath 40, as well as graspers, snares or forceps. The delivery devices can be used alone or through the working channel of an endoscope.

The pylorus plug is attached to a bodily structure such that the pylorus plug is positioned at or adjacent the pylorus 18. Preferably, the pylorus plug is attached directly to the pylorus sphincter 20, although the bodily structure may comprise any of the stomach 14, small intestine 16, or pylorus 18. The attaching step may include expanding a stent, inflating an expandable ring, suturing, anchoring, stapling or similar procedures. Preferably, the attaching step is performed endoscopically utilizing an endoscope or other visualization system (such as a fiber optic catheter-based system). While endoscopic procedures have generally been discussed, it will be recognized that laparoscopic surgery or open surgery may also be performed in order to gain access to the stomach 14 and/or the small intestine 16 for placement of the pylorus plug therebetween. Likewise, when suturing is involved, the suture may be placed endoscopically, laparoscopically, or an open surgery. For example, suturing devices which are capable of cinching tissue in order to allow the formation of pleats in the tissue are well known and may be utilized here. Generally, such devices have a pair of grasping jaws which engage the tissue and form the cinch or pleat, while a suturing needle is passed through the cinched tissue in order to maintain wall apposition. The passageway of the pylorus plug permits a limited amount of stomach contents through the pylorus 18, but preferably reduces a flow rate of stomach contents. Some stomach contents are of course allowed to pass through the pylorus 18 and therefore the flow rate of stomach contents is greater than zero.

It will also be recognized by those skilled in the art that the pylorus plugs as described herein may be configured for permanent implantation or be made so that they are removable after a period of time. For example, the pylorus plug may be constructed of materials which are digestive-resistant, such as the plastics previously discussed or metals such as stainless steel and Nitinol. On the other hand, materials which are known to degrade and pass safely through the body may also be used. Semi-permanent implantations may be designed for later removal, such as by utilizing sutures, snares forceps or the like to collapse the stents or deflectable rings or other structures forming the attachment means as previously described. Similarly, when suture material is used as the attachment means, the suture material may simply be cut or designed to degrade after a period of time. These and other variations of the pylorus plug and method of treating obesity will be readily apparent to those of ordinary skill in the art.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for the treatment of obesity in a patient having a stomach and pylorus leading from the stomach to the intestines, the pylorus having a pyloric sphincter, the medical device comprising:
   a pylorus plug positioned within and engaging the pylorus;
   the pylorus plug having a sleeve of flexible material defining a passageway therethrough, the passageway constructed to delay the emptying of contents from the stomach to the intestines; and
   the pylorus plug having an attachment portion structured to directly engage an interior of the pyloric sphincter, the attachment portion including an expandable member connected to a first end of the sleeve, the expandable member biased to an expanded configuration, the sleeve including a second end located opposite the first end, the second end not attached to the expandable member, wherein pressure from the stomach contents partially closes the passageway adjacent the second end to permit stomach contents to pass from the second end towards the first end, wherein the expandable member biases the first end of the sleeve open, and wherein the second end is not biased either open or closed.

2. The medical device of claim 1, wherein the sleeve projects proximally away from the attachment portion.

3. The medical device of claim 2, wherein the sleeve projects proximally into the stomach.

4. The medical device of claim 1, wherein the passageway of the flexible sleeve, in a fully expanded configuration, has a first area at the first end and a second area at the second end, the second area being smaller than the first area.

5. The medical device of claim 1, wherein the sleeve has sufficient rigidity to prevent inversion.

6. The medical device of claim 1, wherein the sleeve has a generally cylindrical shape.

7. The medical device of claim 1, wherein the sleeve has a generally frustoconical shape.

8. The medical device of claim 7, wherein the sleeve projects away from the attachment portion and into the intestines.

9. The medical device of claim 1, wherein the expandable member is an expandable stent.

* * * * *